US009631033B2

(12) United States Patent
Takaki

(10) Patent No.: US 9,631,033 B2
(45) Date of Patent: Apr. 25, 2017

(54) N-PHENYLMALEIMIDE COMPOUND AND COPOLYMER COMPOSITION OBTAINED USING SAME

(75) Inventor: Hiroyuki Takaki, Himeji (JP)

(73) Assignee: NIPPON SHOKUBAI CO., LTD., Osaki-Shi, Osaka (JP)

( * ) Notice: Subject to any disclaimer, the term of this patent is extended or adjusted under 35 U.S.C. 154(b) by 0 days.

(21) Appl. No.: 14/006,751

(22) PCT Filed: Mar. 19, 2012

(86) PCT No.: PCT/JP2012/057029
§ 371 (c)(1),
(2), (4) Date: Sep. 23, 2013

(87) PCT Pub. No.: WO2012/128255
PCT Pub. Date: Sep. 27, 2012

(65) Prior Publication Data
US 2014/0011959 A1   Jan. 9, 2014

(30) Foreign Application Priority Data

Mar. 24, 2011 (JP) ................. 2011-065547

(51) Int. Cl.
C08L 55/02 (2006.01)
C08C 19/28 (2006.01)
C07D 207/448 (2006.01)
C08F 236/12 (2006.01)
C08F 222/40 (2006.01)
C08F 279/02 (2006.01)

(52) U.S. Cl.
CPC .......... C08C 19/28 (2013.01); C07D 207/448 (2013.01); C08F 222/40 (2013.01); C08F 236/12 (2013.01); C08F 279/02 (2013.01); C08L 55/02 (2013.01)

(58) Field of Classification Search
CPC ... C08F 2220/40; C08L 55/02; C07D 207/448
See application file for complete search history.

(56) References Cited

U.S. PATENT DOCUMENTS

| 4,904,803 | A |   | 2/1990 | Fujita et al. |
| 5,128,484 | A |   | 7/1992 | Kita et al. |
| 5,136,052 | A | * | 8/1992 | Van Gysel et al. ............ 548/549 |
| 5,262,504 | A |   | 11/1993 | Tazaki et al. |
| 5,310,831 | A |   | 5/1994 | Maeda et al. |
| 5,478,903 | A |   | 12/1995 | Fujioka et al. |
| 5,556,991 | A | * | 9/1996 | Kita et al. ..................... 548/548 |
| 2005/0182260 | A1 |   | 8/2005 | Mederski et al. |

FOREIGN PATENT DOCUMENTS

| EP | 0627420 A1 | 12/1994 |
| JP | 62-77364 A | 4/1987 |
| JP | 1-250348 A | 10/1989 |
| JP | 1-283264 A | 11/1989 |
| JP | 2-28150 A | 1/1990 |
| JP | 02-028150 A | 1/1990 |
| JP | 03-56463 A | 3/1991 |
| JP | 3-56463 A | 3/1991 |
| JP | 4-209868 A | 7/1992 |
| JP | 4-221365 A | 8/1992 |
| JP | 04-221365 A | 8/1992 |
| JP | 04-243864 A | 8/1992 |
| JP | 4-243864 A | 8/1992 |
| JP | 04-290868 A | 10/1992 |
| JP | 4-295462 A | 10/1992 |
| JP | 04-295462 A | 10/1992 |
| JP | 5-25129 A | 2/1993 |
| JP | 5-140095 A | 6/1993 |
| JP | 6-135931 A | 5/1994 |
| JP | 6-184105 A | 7/1994 |
| JP | 8-27108 A | 1/1996 |
| JP | 2009-126866 A | 6/2009 |
| KR | 20090074982 A | 7/2009 |

OTHER PUBLICATIONS

Notification Concerning Transmittal of International Preliminary Report on Patentability (Form PCT/IB/326 and PCT/IB/373) dated Oct. 3, 2013, issued in corresponding International Application No. PCT/JP2012/057029 (7 pgs.).

Notification of Transmittal of Translation of the International Preliminary Report on Patentability (Form PCT/IB/338 and PCT/IB/373) and the Written Opinion of the International Searching Authority (Forms PCT/ISA/237) dated Oct. 3, 2013, issued in corresponding International Application No. PCT/JP2012/057029 (9 pgs.).

International Search Report (PCT/ISA/210) mailed on May 1, 2012, by the Japanese Patent Office as the International Searching Authority for International Application No. PCT/JP2012/057029.

Written Opinion (PCT/ISA/237) mailed on May 1, 2012, by the Japanese Patent Office as the International Searching Authority for International Application No. PCT/JP2012/057029.

EPO Form 1201 dated Jul. 31, 2013, by the Japanese Patent Office as the International Searching Authority for International Application No. PCT/JP2012/057029.

Office Action (Notice of Reason(s) for Refusal) issued on Jun. 10, 2014, by the Japanese Patent Office in corresponding Japanese Patent Application No. 2013-505968, and an English Translation of the Office Action. (7 pages).

Extended European Search Report issued in corresponding European Patent Application No. 12760753.9 dated Nov. 7, 2014, 7 pages.

(Continued)

*Primary Examiner* — Mark Kaucher
(74) *Attorney, Agent, or Firm* — Buchanan Ingersoll & Rooney PC

(57) ABSTRACT

The present invention provides an N-phenylmaleimide compound that can improve the quality of the obtained copolymer by using N-phenylmaleimide containing impurities in specific amounts or less as at least one component of the copolymerization monomers. The N-phenylmaleimide compound of the present invention contains 0.1% by weight or less of N-(2,5-dioxo-1-phenyl-3-pyrrolidinyl)-N-phenylmaleamic acid (PPMA) and/or 0.3% by weight or less of N-phenylfumaramic acid (PFA).

16 Claims, No Drawings

(56) References Cited

OTHER PUBLICATIONS

Chinese Office Action issued in corresponding Chinese Patent Application No. 201280004921.4 dated Nov. 13, 2014, 6 pages.
Kita et al., "Mechanism of the Synthesis of N-Phenylmaleimide and Improvement of its Selectivity", The Chemical Society of Japan, No. 4, pp. 375-384 (with English abstract and partial English translation).
Taiwanese Office Action issued in Taiwanese Patent Application No. 101109196, dated Jul. 8, 2015 (with partial English translation).
Chinese Office Action issued in corresponding Chinese Patent Application No. 201280004921.4 dated Aug. 26, 2015 (with partial English translation).
Office Action dated Feb. 3, 2016, issued by the State Intellectual Property Office of China in corresponding Chinese Patent Application No. 201280004921.4, and a partial English translation of the Office Action. (6 pages).
Notice of Reason for Refusal dated Aug. 2, 2016, issued by the Japanese Patent Office in corresponding Japanese Patent Application No. 2013-505968, and an English translation of the Office Action.

\* cited by examiner

N-PHENYLMALEIMIDE COMPOUND AND COPOLYMER COMPOSITION OBTAINED USING SAME

TECHNICAL FIELD

The present invention relates to an N-phenylmaleimide compound and a copolymer composition obtained using the same. More specifically, it relates to an N-phenylmaleimide compound having a low content of the compound necessarily generated when a maleimide compound is produced, and a copolymer composition obtained by copolymerization using the N-phenylmaleimide compound as at least one component of monomers.

BACKGROUND ART

A maleimide compound is a compound useful as an ingredient of resin, an ingredient of pharmaceuticals and pesticides, and the like, and often used as one of copolymerization components for improvement in heat resistance of, particularly, styrene-based resins such as ABS resins, AS resins, AB resins, ACS resins, AES resins and AAS resins, and polyvinyl chloride resins, polymethyl methacrylate resins, phenol resins, and the like. Among them, N-phenylmaleimide (hereinafter also referred to as PMI) is excellent in reactivity and heat resistance, and thus especially widely used.

As the method for producing a maleimide compound, many methods such as a method of obtaining by dehydrating maleic anhydride and a primary amine in one step (for example, Patent Literatures 1 and 2), a method of producing a maleamic acid from maleic anhydride and a primary amine and obtaining by a dehydration ring-closure imidization reaction of the maleamic acid (for example, Patent Literatures 3 to 6) and a method of obtaining by a ring-closure imidization reaction of a corresponding maleamic monoester (for example, Patent Literatures 7 to 9) are conventionally known. Among these methods, the method of obtaining by dehydrating maleic anhydride and a primary amine in one step has a problem that the yield is still low and thus the productivity is low, and the method of obtaining from a maleamic monoester has a problem that an alcohol generated by the ring-closure imidization remains and contaminates in the product, thus the method of obtaining by the dehydration ring-closure imidization reaction of a maleamic acid is generally industrially carried out. Here, when producing N-phenylmaleimide, the primary amine is aniline, and the maleamic acid is N-phenylmaleamic acid.

Incidentally, when producing N-phenylmaleimide according to the above method, it goes through the generation of N-phenylmaleamic acid (hereinafter also referred to as PMA) as an intermediate, and when this PMA is hydrolyzed, aniline and a maleic acid are produced. It is known that the produced aniline (or aniline derived from raw materials) reacts with the PMI of target product to produce 2-anilino-N-phenylsuccinimide (hereinafter also referred to as APSI), this APSI further reacts with maleic anhydride to produce N-(2,5-dioxo-1-phenyl-3-pyrrolidinyl)-N-phenylmaleamic acid (hereinafter also referred to as PPMA), and this PPMA further decomposes to produce PMI. It is also known that PMA is isomerized to produce N-phenylfumaramic acid (hereinafter also referred to as PFA). When PMI in which the intermediates and the by-products thereof are present as impurities is used, as one of the copolymerization components for obtaining the resin product as described above, there are problems that the obtained copolymer is colored or discolors, or the deterioration in qualities (heat resistance and strength) of the copolymer occurs by causing phenomena such as silver streak and fish eye, and the like.

In order to solve these problems, for example, Patent Literature 3 discloses a method of reducing acid components (PMA, maleic anhydride, and fumaric acid) in the maleimide by separating a reaction mixture after ring-closure imidization into the organic solvent layer containing the maleimide and the catalyst layer, subjecting the maleimide-containing organic solvent layer to the water washing treatment at a temperature of 70° C. or more, then separating the organic solvent layer and the aqueous layer. In addition, for example, Patent Literature 10 discloses a method for producing N-substituted maleimide having a purity of 95% by weight or more by adding a primary amine and maleic anhydride, in the presence of an organic solvent that can be azeotropically distilled with water and a supported catalyst where an organic phosphonic acid having a melting point of 150° C. or more and insoluble with the N-substituted maleimide is supported on a solid carrier, to carry out a dehydration ring closure reaction at 100 to 140° C.

Furthermore, for example, Patent Literature 11 discloses that, in the storage stabilization method that prevents color change by adjusting the contents of a primary amine and 2-amino-N-substituted succinimide compound in the maleimide compound to specific amounts or less, as a method of adjusting the amount of the 2-amino-N-substituted succinimide compound, the production of 2-amino-N-substituted succinimide compound can be suppressed by controlling the molar ratio of maleic anhydride and the primary amine during the reaction or by adding maleic anhydride in the latter half of the reaction to decompose the 2-amino-N-substituted succinimide compound.

CITATION LIST

Patent Literatures

Patent Literature 1: JP-A-H05-25129
Patent Literature 2: US Patent Application Publication No. 2005/182,260
Patent Literature 3: JP-A-H03-56463
Patent Literature 4: JP-A-H04-243864
Patent Literature 5: JP-A-H04-295462
Patent Literature 6: JP-A-H05-140095
Patent Literature 7: JP-A-H04-221365
Patent Literature 8: JP-A-H04-290868
Patent Literature 9: JP-A-H06-184105
Patent Literature 10: JP-A-2009-126866
Patent Literature 11: JP-A-H06-135931

SUMMARY OF INVENTION

Technical Problem

However, even in the case of using the N-phenylmaleimide obtained by these methods, it is often still inadequate to solve the problems in the resin products described above.

As described above, in the copolymer using N-phenylmaleimide as at least one component of the copolymerization monomers, it cannot be necessarily satisfied in terms of improvement in quality at present. The cause of this situation is assumed to be derived from impurities contained in N-phenylmaleimide, and thus it is necessary to reduce the content thereof to a desired level.

Specifically, the present invention has been made in view of the above situations, and an object of the present invention is to identify the types and amounts of the impurities contained in an N-phenylmaleimide compound that affect the quality of the obtained copolymer.

Another object of the present invention is to provide an N-phenylmaleimide compound containing specific impurities in specific amounts or less.

A further object of the present invention is to provide a copolymer composition improved in the quality of the obtained copolymer by using an N-phenylmaleimide compound containing specific impurities in specific amounts or less as at least one component of the copolymerization monomers

.

Solution to Problem

To solve the above problems, the present inventors have intensively studied the effect of impurities in an N-phenylmaleimide compound used as at least one component of the copolymerization monomers. As a result, the present inventors have found that the quality of the copolymer obtained using the N-phenylmaleimide compound can be improved by setting the contents of specific impurities, specifically, N-(2,5-dioxo-1-phenyl-3-pyrrolidinyl)-N-phenylmaleamic acid (PPMA) to 0.1% by weight or less and/or N-phenylfumaramic acid (PFA) to 0.3% by weight or less in the N-phenylmaleimide compound, whereby the present invention is completed.

Specifically, the above purposes can be accomplished by an N-phenylmaleimide compound containing 0.1% by weight or less of N-(2,5-dioxo-1-phenyl-3-pyrrolidinyl)-N-phenylmaleamic acid (PPMA) and/or 0.3% by weight or less of N-phenylfumaramic acid (PFA).

The above purposes can also be accomplished by a copolymer composition obtained by copolymerizing the N-phenylmaleimide compound and one or more other monomers or resins copolymerizable with the N-phenylmaleimide compound.

Advantageous Effects of Invention

According to the present invention, an N-phenylmaleimide compound in which the content of impurities is reduced is obtained. When the N-phenylmaleimide compound as described above is used, phenomena such as coloring, silver streak and fish eye of the obtained copolymer are reduced, thus the qualities (for example, appearance, heat resistance, and strength) of the copolymer are improved. The copolymer composition obtained by the present invention is excellent in appearance, heat resistance, and strength, thus can be suitably used as a heat-resistant resin in a wide variety of fields. Furthermore, the copolymer composition obtained by the present invention can be suitably used on various applications in which a heat-resistant resin is utilized including the fields of automobiles and household appliances, specifically as a modified heat resistant resin of an AB resin, ABS resin, or AS resin.

DESCRIPTION OF EMBODIMENTS

A first aspect of the present invention relates to an N-phenylmaleimide compound (hereinafter also simply referred to as N-phenylmaleimide or PMI) containing 0.1% by weight or less of N-(2,5-dioxo-1-phenyl-3-pyrrolidinyl)-N-phenylmaleamic acid (PPMA) and/or 0.3% by weight or less of N-phenylfumaramic acid (PFA). When N-phenylmaleimide is industrially produced, it is very difficult to obtain an "absolutely pure" N-phenylmaleimide not containing other substances at all, and N-phenylmaleimide containing various substances as impurities is generally obtained. Therefore, in the present invention, among substances contained in N-phenylmaleimide, specifically, a substance that is the cause of the problem when N-phenylmaleimide is used for various uses and the amount thereof (critical amount) are specified for the first time.

Incidentally, in the present specification, "N-phenylmaleimide compound" refers to those substantially constituted by N-phenylmaleimide. Specifically, the N-phenylmaleimide compound according to the present invention refers to those having a purity of N-phenylmaleimide of 96% by weight or more. The N-phenylmaleimide compound according to the present invention has a purity of N-phenylmaleimide of preferably 97% by weight or more, more preferably 98% by weight or more, and particularly preferably 99% by weight or more. Therefore, the N-phenylmaleimide compound according to the present invention includes various forms such as N-phenylmaleimide products, N-phenylmaleimide crude products, N-phenylmaleimide purified products, N-phenylmaleimide raw materials, N-phenylmaleimide raw materials and N-phenylmaleimide materials, having a purity of 96% by weight or more. In the specification of the present application, "mass" and "weight", "% by mass" and "% by weight", and "part by mass" and "part by weight" are synonyms.

Hereinafter, the present invention will be described in detail.

The method for producing an N-substituted maleimide compound represented by N-phenylmaleimide includes the methods as described in the above references and the like and is not particularly limited. Specifically, there are methods such as (a) a method of obtaining by dehydrating maleic anhydride and a primary amine in one step; (b) a method of producing a maleamic acid from maleic anhydride and a primary amine and obtaining by a dehydration ring-closure imidization reaction of the maleamic acid; (c) a method of obtaining by a ring-closure imidization reaction of a corresponding maleamic monoester; and the like. Among them, the method of (b) is preferable, namely, for example, as the method for producing an N-phenylmaleimide, a method of reacting maleic anhydride and aniline as raw materials to produce an N-phenylmaleamic acid (PMA) and allowing the N-phenylmaleamic acid to undergo a dehydration ring-closure imidization reaction is particularly preferable.

In producing an N-phenylmaleimide by the method of (b), aniline and maleic acid are produced by hydrolysis of N-phenylmaleamic acid (PMA) as an intermediate. The produced aniline or aniline derived from raw materials reacts with N-phenylmaleimide of the target product to produce 2-anilino-N-phenylsuccinimide (APSI). In addition, this APSI further reacts with maleic anhydride derived from raw materials to produce N-(2,5-dioxo-1-phenyl-3-pyrrolidinyl)-N-phenylmaleamic acid (PPMA). Furthermore, the N-phenylmaleamic acid (PMA) is isomerized to produce N-phenylfumaramic acid (PFA) (see the following reaction formula).

[Formula 1]
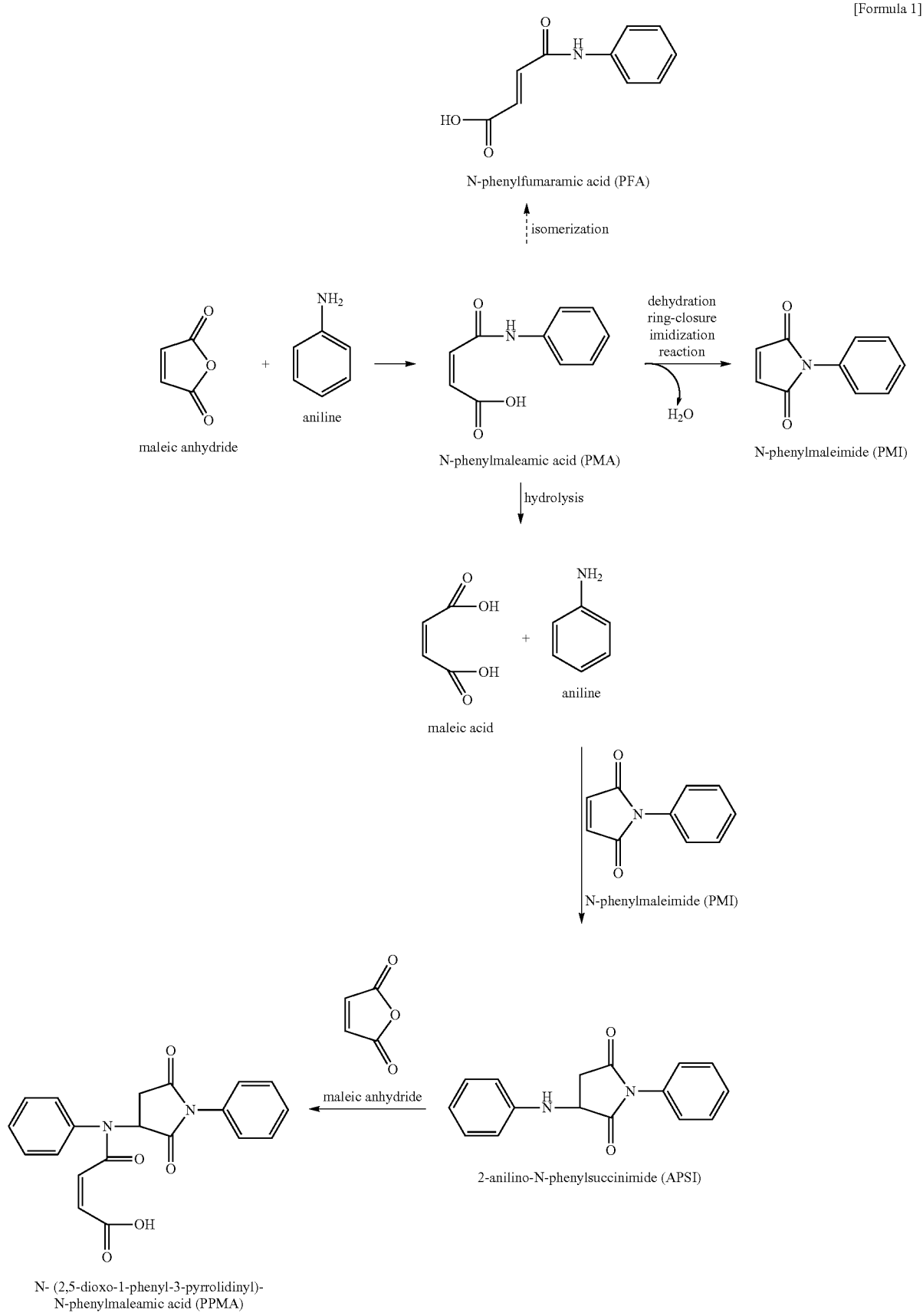

Here, N-phenylmaleimide (PMI) according to the present invention is a compound having a chemical structure represented by the following formula.

[Formula 2]

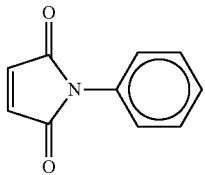

In addition, N-(2,5-dioxo-1-phenyl-3-pyrrolidinyl)-N-phenylmaleamic acid (PPMA) according to the present invention is a compound having a chemical structure represented by the following formula.

[Formula 3]

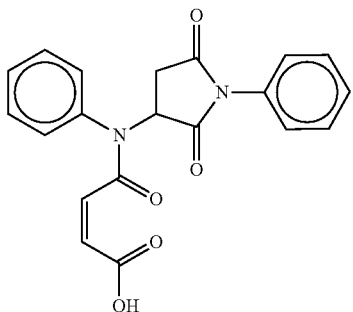

In addition, N-phenylfumaramic acid (PFA) according to the present invention is a compound having a chemical structure represented by the following formula.

[Formula 4]

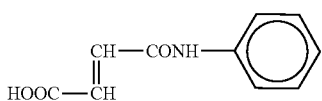

In addition, N-phenylmaleamic acid (PMA) according to the present invention is a compound having a chemical structure represented by the following formula.

[Formula 5]

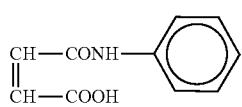

In addition, 2-anilino-N-phenylsuccinimide (APSI) according to the present invention is a compound having a chemical structure represented by the following formula.

[Formula 6]

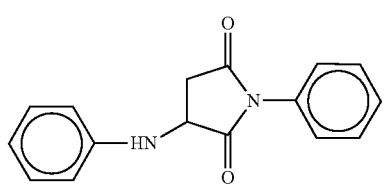

As described above, PMA as an intermediate undergoes a dehydration ring-closure imidization reaction to obtain PMI of a target product, or undergoes hydrolysis reaction to produce aniline and maleic acid or is isomerized to produce PFA as a by-product. However, PMA in the entire amount does not necessarily undergo one of the reactions to be completely changed, and each of the products is present as impurities in the PMI. In addition, it is not easy that the APSI produced by the reaction of PMI with aniline decomposes to return again to the PMI in the production process. Therefore, a method of further introducing excess maleic anhydride to the reaction system, thereby obtaining PPMA in which decomposition reaction to PMI is likely to proceed, as compared with APSI, to obtain PMI through PPMA, is generally often adopted. However, in the reaction from APSI to PPMA, and also the decomposition reaction from PPMA to PMI, these in the entire amount do not necessarily be changed completely, thus APSI and PPMA are also present as impurities in PMI. In addition, by this isomerization of PMA, N-phenylfumaramic acid (PFA) is also produced, and it is not easy that PFA in the entire amount is reisomerized to return again to PMI in the production process, thus the PFA is also present as impurities in PMI.

As described above, the N-phenylmaleimide compound (PMI) according to the present invention contains PPMA, PFA, PMA and APSI as impurities. When PMI containing these impurities is used as one component of the copolymerization monomers, the qualities such as appearance, heat resistance and strength may be deteriorated as described above, thus it is desirable to reduce the content of these impurities as much as possible.

In the present invention, it has been found for the first time that the contents of especially PPMA and PFA, among the impurities described above, affect the qualities (for example, appearance, heat resistance, strength and the like) of the copolymer obtained using the N-phenylmaleimide compound, and also, the upper limits of the contents of these impurities that affect to the qualities of the copolymer have been found for the first time. Specifically, the N-phenylmaleimide compound of the present invention is characterized by containing 0.1% by weight or less of PPMA or 0.3% by weight or less of PFA based on the entire amount of the N-phenylmaleimide compound. The content of PPMA or PFA in the N-phenylmaleimide compound should satisfy at least one content, and preferably satisfies both of the contents.

Therefore, in the present invention, N-phenylmaleimide (PMI) containing 0.1% by weight or less of N-(2,5-dioxo-1-phenyl-3-pyrrolidinyl)-N-phenylmaleamic acid (PPMA) and/or 0.3% by weight or less of N-phenylfumaramic acid (PFA) is used as at least one component of the copolymerization monomers.

The content of PPMA in the N-phenylmaleimide compound is 0.1% by weight or less based on the entire amount of the N-phenylmaleimide compound. Here, when the N-phenylmaleimide compound containing PPMA of the content over 0.1% by weight is used as one component of the copolymerization monomers, it is not preferable since the qualities such as appearance, heat resistance and strength of the produced copolymer are deteriorated. The content of PPMA in the N-phenylmaleimide compound is preferably 0.09% by weight or less, more preferably 0.08% by weight or less, further preferably 0.06% by weight or less, further more preferably 0.03% by weight or less, and particularly preferably 0.01% by weight or less, based on the entire amount of the N-phenylmaleimide compound. Here, it is preferable that the lower limit of the content of PPMA in the N-phenylmaleimide compound is as smaller as possible (specifically, 0% by weight). From the industrial viewpoint, the lower limit is normally above 0% by weight and preferably 0.005% by weight or more. In the present specification, the content of PPMA is the value measured in the following Examples.

In addition, the content of PFA in the N-phenylmaleimide compound is 0.3% by weight or less based on the entire amount of the N-phenylmaleimide compound. Here, when the N-phenylmaleimide compound containing PFA of the content over 0.3% by weight is used as one component of the copolymerization monomers, it is not preferable since the qualities such as appearance, heat resistance and strength of the produced copolymer are deteriorated. The content of PFA in the N-phenylmaleimide compound is preferably, in order, 0.25% by weight or less, 0.2% by weight or less, 0.15% by weight or less, and 0.1% by weight or less, based on the entire amount of the N-phenylmaleimide compound. Here, it is preferable that the lower limit of the content of PFA in the N-phenylmaleimide compound is as smaller as possible (specifically, 0% by weight). From the industrial viewpoint, the lower limit is normally above 0% by weight and preferably 0.01% by weight or more. In the present specification, the content of PFA is the value measured in the following Examples.

In addition to the above, it has been found that the PMA and APSI also affect the qualities (for example, appearance, heat resistance, strength, and the like) of the copolymer obtained using the N-phenylmaleimide compound, and the upper limits of the contents of these impurities that affect to the qualities of the copolymer have been found. Specifically, the N-phenylmaleimide compound of the present invention contains PMA and APSI, and the total content of PMA, APSI, PPMA and PFA in the N-phenylmaleimide compound is preferably 0.5% by weight or less, based on the entire amount of the N-phenylmaleimide compound. Here, when the N-phenylmaleimide compound containing PMA, APSI, PPMA and PFA of the total content more than 0.5% by weight is used as one component of the copolymerization monomers, it is not preferable since the qualities such as appearance, heat resistance and strength of the produced copolymer are deteriorated. The total content of PMA, APSI, PPMA and PFA in the N-phenylmaleimide compound is preferably, in order, 0.4% by weight or less, 0.3% by weight or less, 0.25% by weight or less, and 0.2% by weight or less, based on the entire amount of the N-phenylmaleimide compound. Here, it is preferable that the lower limit of the total content of PMA, APSI, PPMA and PFA in the N-phenylmaleimide compound is as smaller as possible (specifically, 0% by weight). From the industrial viewpoint, the lower limit is normally above 0% by weight and preferably 0.1% by weight or more.

Incidentally, the total content of PMA, APSI and PPMA in the N-phenylmaleimide compound is not particularly limited as long as the total content satisfies the above requirements. Specifically, the total content of PMA, APSI and PPMA in the N-phenylmaleimide compound is preferably, in order, 0.35% by weight or less, 0.3% by weight or less, 0.25% by weight or less, 0.2% by weight or less, 0.15% by weight or less, 0.1% by weight or less, 0.05% by weight or less, and 0.03% by weight or less. Here, it is preferable that the lower limit of the total content of PMA, APSI and PPMA in the N-phenylmaleimide compound is as smaller as possible (specifically, 0% by weight). From the industrial viewpoint, the lower limit is normally above 0% by weight and preferably 0.1% by weight or more.

Here, the content of PMA in the N-phenylmaleimide compound is not particularly limited as long as the content satisfies the above requirements. Specifically, the content of PMA in the N-phenylmaleimide compound is preferably 0.2% by weight or less, more preferably 0.1% by weight or less, further preferably 0.07% by weight or less, further more preferably 0.05% by weight or less, and particularly preferably 0.02% by weight or less, based on the entire amount of the N-phenylmaleimide compound. Here, it is preferable that the lower limit of the content of PMA in the N-phenylmaleimide compound is as smaller as possible (specifically, 0% by weight). From the industrial viewpoint, the lower limit is normally above 0% by weight and preferably 0.005% by weight or more. In the present specification, the content of PMA is the value measured in the following Examples.

Also, the content of APSI in the N-phenylmaleimide compound is not particularly limited as long as the content satisfies the above requirements. Specifically, the content of APSI in the N-phenylmaleimide compound is preferably, in order, 0.2% by weight or less, 0.15% by weight or less, 0.1% by weight or less, 0.05% by weight or less, 0.03% by weight or less, and 0.01% by weight or less, based on the entire amount of the N-phenylmaleimide compound. Here, it is preferable that the lower limit of the content of APSI in the N-phenylmaleimide compound is as smaller as possible (specifically, 0% by weight). From the industrial viewpoint, the lower limit is normally above 0% by weight and preferably 0.02% by weight or more. In the present specification, the content of APSI is the value measured in the following Examples.

The PMI in which these impurities are reduced to the above-described ranges is used as one component of the copolymerization monomers, whereby the quality issues of the above-described copolymers, specifically resin products, can be improved. Here, the purity of the PMI comprising the above-described impurities is preferably, in order, 96% by weight or more, 97% by weight or more, 98% by weight or more, 98.5% by weight or more, 99% by weight or more, 99.5% by weight or more, more than 99.5% by weight, 99.7% by weight or more, and 99.8% by weight or more. In the present specification, the purity of the PMI is the value measured in the following Examples.

The method for producing an N-substituted maleimide compound represented by N-phenylmaleimide is not particularly limited as described above, and known methods such as the methods as described in the above references and the like are applicable in the same manner or with appropriate modifications. Specifically, there are methods such as (a) a method of obtaining by dehydrating maleic anhydride and a primary amine in one step; (b) a method of producing maleamic acid from maleic anhydride and a primary amine and obtaining by a dehydration ring-closure imidization reaction of the maleamic acid; (c) a method of obtaining by a ring-closure imidization reaction of a corresponding maleamic monoester; and the like. Among them, the method of (b) is preferable, namely, for example, as the method for producing an N-phenylmaleimide, a method of reacting maleic anhydride and aniline as raw materials to produce N-phenylmaleamic acid (PMA) and allowing N-phenylmaleamic acid to undergo a dehydration ring-closure imidization reaction is particularly preferable. Hereinafter, preferable embodiments of the method (b) will be described in detail, but the present invention is not limited to the following embodiments.

As the method for producing PMI according to the present invention, first, N-phenylmaleamic acid is obtained from maleic anhydride and aniline and is allowed to undergo the ring-closure imidization (dehydration ring-closure imidization reaction) to produce PMI. In more detail, aniline is added to maleic anhydride to obtain N-phenylmaleamic acid. Next, the obtained N-phenylmaleamic acid is heated in an organic solvent in the presence of an acid catalyst, and is allowed to undergo the ring-closure imidization reaction while the produced water is distilled away outside the system as a mixture with the organic solvent, to obtain PMI. In this case, the reaction is carried out with the molar ratio of the entire amount of maleic anhydride added to the reaction system is more than 1, and 2 or less, and preferably more than 1, and 1.3 or less, based on the entire amount of aniline added to the reaction system.

In addition, in the step of obtaining N-phenylmaleamic acid from maleic anhydride and aniline, maleic anhydride or aniline may be used in the form as it is, and is preferably used in the form of a solution obtained by dissolving it in an organic solvent. When maleic anhydride or aniline is used in the form of a solution obtained by dissolving it in an organic solvent, the next dehydration ring-closure imidization reaction of N-phenylmaleamic acid can directly be carried out in the solution (organic solvent).

The organic solvent that can be used when producing PMI is not particularly limited, and a solvent that is insoluble or immiscible in water and inactive (not involved in the reaction) is preferable. Examples of the solvent described above include benzene, toluene, oil fractions having a boiling point of 50 to 120° C., xylene, ethylbenzene, isopropylbenzene, cumene, mesitylene, tert-butylbenzene, pseudocumene, trimethylhexane, octane, tetrachloroethane, nonane, chlorobenzene, ethylcyclohexane, oil fractions having a boiling point of 120 to 170° C., m-dichlorobenzene, sec-butylbenzene, p-dichlorobenzene, decane, p-cymene, o-dichlorobenzene, butylbenzene, decahydronaphthalene, tetrahydronaphthalene, dodacane, naphthalene, cyclohexylbenzene, oil fractions having a boiling point of 170 to 250° C., and the like. The organic solvents may be used singly or in the form of a mixture of two or more thereof.

The amount of the organic solvent is not particularly limited, and from the viewpoint of smoothly carrying out the reaction and satisfying economic conditions, the organic solvent is used in an amount of 0.5 to 20 times by weight and preferably 1 to 7 times by weight, based on the total amount of maleic anhydride and aniline that are raw materials. In addition, an organic solvent having a boiling point appropriate for the reaction conditions also is selected considering solubility of PMI, price, handling properties and the like. Further, when considering separation of PMI from the solvent after the completion of the reaction, there also may be a case where it is more advantageous when the reaction is carried out under pressure using a solvent having low boiling point. Here, maleic anhydride and aniline may be dissolved in the same organic solvent or dissolved in different organic solvents, and is preferably dissolved in the same organic solvent. Also, the concentration of maleic anhydride or aniline, when maleic anhydride or aniline is used in the form of the solution dissolved in an organic solvent, is not particularly limited as long as maleic anhydride or aniline is soluble. Specifically, it is preferred that 0 to 500 g and more preferably 10 to 200 g of the organic solvent be added to and dissolved in 100 g of maleic anhydride. Also, it is preferred that 0 to 500 g and more preferably 5 to 200 g of the organic solvent be added to and dissolved in 100 g of aniline.

In addition, the conditions when aniline is added to maleic anhydride are not particularly limited. For example, the addition temperature is preferably about 50 to 140° C. Also, the addition time is preferably about 10 to 120 minutes.

N-phenylmaleamic acid obtained as described above is heated in an organic solvent, preferably in the presence of an acid catalyst, and is allowed to undergo the ring-closure imidization (dehydration ring-closure imidization reaction) while the produced water is distilled away outside the system as a mixture with the organic solvent, to obtain desired N-phenylmaleimide (PMI).

Here, the organic solvent similar to the organic solvent described above can be used. In addition, when maleic anhydride or aniline is used in the form of a solution obtained by dissolving in an organic solvent, the next dehydration ring-closure imidization reaction of N-phenylmaleamic acid can directly be carried out in the solution (organic solvent).

Also, as the acid catalyst, a monobasic acid or polybasic acid such as sulfuric acid, orthophosphoric acid, metaphosphoric acid or pyrophosphoric acid, and/or an amine salt obtained by neutralizing aniline that is a raw material for producing PMI with the acid are used. These catalysts are used in the range of 1 to 200% by mol and preferably 10 to 100% by mol, based on maleic anhydride and/or aniline that are raw materials. Also, apart or all of the acids as a catalyst may be neutralized by amine.

In addition, these catalysts may be supported on a solid carrier. As the solid carrier, natural minerals, for example, kaolin, clay, talc, chalk, quartz, bentonite, montmorillonite, diatomaceous earth, and the like; synthetic minerals, for example, highly dispersed silicic acid, alumina, silicate, activated carbon, plaster, colcothar, titanium oxide, silica, silica-alumina, zirconium oxide, and the like; natural rocks, for example, calcite, marble, pumice, meerschaum, dolomite, and the like, are used. These inorganic carriers are used in the form of a granulate, or a granulate obtained by granulating and classifying the inorganic carriers, or a honeycomb form or the like. In addition, an organic carrier can also be used, and granulated carriers such as polyfluorocarbon, polystyrene and phenol resin can also be used. When the carrier is porous like diatomaceous earth, silica gel and the like, particularly good result can be obtained. For example, examples of a commercially available product include radio light (trade name; manufactured by Showa Chemical Industry Co., Ltd.) as diatomaceous earth, CARiACT (trade name; manufactured by Fuji Silysia chemical Ltd.), syloid (trade name; manufactured by Fuji Silysia chemical Ltd.), microbead silica gel (trade name; manufactured by Fuji Silysia chemical Ltd.) and Wako-gel (trade name; manufactured by Wako Pure Chemical Industries, Ltd.) as silica gel, and the like.

Optionally, the reaction can be carried out with the coexistence of a metal-containing compound and a stabilizer in the reaction system. The metal-containing compound used is not particularly limited, and includes metal oxides, acetates, maleates, succinates, nitrates, phosphates, chlorides and sulfates of at least one selected from the group consisting of zinc, chromium, palladium, cobalt, nickel, iron and aluminum, and the like. Among them, particularly effective compound is zinc acetate. These compounds are used in an amount of 0.005 to 0.5% by mol and preferably 0.01 to 0.1% by mol as a metal, based on maleic anhydride and/or aniline that are raw materials.

In addition, as the stabilizer, methoxybenzoquinone, p-methoxyphenol, phenothiazine, hydroquinone, alkylated diphenylamine, methylene blue, tert-butylcatechol, tert-butylhydroquinone, zinc dimethyldithiocarbamate, copper dimethyldithiocarbamate, copper dibutyldithiocarbamate, copper salicylate, thiodipropionate ester, mercaptobenzimidazole, triphenyl phosphite, alkylphenol, alkylbisphenol and the like are used. These stabilizers plays a role in allowing the PMI produced by dehydration ring-closure imidization reaction to stably exist without changing in quality even under high temperature of the imidization reaction. The addition amount thereof is not particularly limited, and is 0.001 to 0.5% by mol, based on maleic anhydride and/or aniline that are raw materials. Here, when the addition amount is as described above, the stabilizer can sufficiently exhibit the stabilization effect described above, and the problem of contamination into the product can be avoided.

The conditions for the dehydration ring-closure imidization reaction are not particularly limited as long as the ring-closure imidization reaction of N-phenylmaleamic acid proceeds. Specifically, the temperature of the dehydration ring-closure imidization reaction is preferably 150° C. or less, more preferably 20 to 140° C., and particularly preferably 30 to 120° C. In addition, the time for the dehydration ring-closure imidization reaction is preferably 10 to 200 minutes and more preferably 15 to 120 minutes. When the reaction conditions are as described above, the dehydration ring-closure imidization reaction of N-phenylmaleamic acid efficiently proceeds, and N-phenylmaleimide (PMI) can be efficiently obtained.

In addition, it is also possible to additionally add a part of maleic anhydride in the course of the dehydration ring-closure imidization reaction. Maleic anhydride is additionally added, whereby the contents of PPMA and PFA, furthermore APSI and PMA, in the obtained PMI can be reduced. Here, the amount of maleic anhydride additionally added is not particularly limited, and is preferably 5 to 50 g and more preferably 10 to 30 g, based on 100 g of the maleic anhydride used in the initial reaction step for obtaining N-phenylmaleamic acid. When the amount is as described above, the contents of PPMA and PFA, furthermore APSI and PMA, in PMI can be effectively reduced. At that time, maleic anhydride may be used in the form as it is, and is preferably used in the form of a solution obtained by dissolving in an organic solvent. The organic solvent that can be used in the latter case is not particularly limited, and the organic solvent similar to those described above can be used. Preferably, the organic solvent as same as the one that dissolves maleic anhydride in the initial reaction step is used.

The concentration of maleic anhydride when the additionally added maleic anhydride which is used in the form of the solution dissolved in an organic solvent is not particularly limited as long as maleic anhydride is soluble. Specifically, it is preferred that 0 to 500 g and more preferably 10 to 200 g of the organic solvent be added to and dissolved in 100 g of maleic anhydride. When the amount is as described above, the contents of PPMA and PFA, furthermore APSI and PMA, in PMI can be effectively reduced.

The timing of additionally adding maleic anhydride (or a solution thereof) is not particularly limited. Specifically, the timing is preferably after 5 to 120 minutes and more preferably after 10 to 60 minutes from when N-phenylmaleamic acid is mixed with a catalyst (when the reaction is started). When the timing is as described above, the contents of PPMA and PFA, furthermore APSI and PMA, in PMI can be effectively reduced. The additional addition of maleic anhydride (or a solution thereof) may be carried out at one time or may be carried out in plural times (for example, 2 to 5 times), and is preferably carried out at one time.

Although the PMI obtained as described above can be used even directly for the production of the copolymer of the present invention, it is preferred that the purification step be further applied since highly pure PMI having less contents of PPMA and PFA, further APSI and PMA, according to the present invention, can be obtained. As the purification method, it can also be obtained by conventionally known purification methods such as the methods described in the above-described patent literatures, and it is preferred that the purification step be repeated or the purification conditions be made more strict since it can be stably and efficiently obtained for a long term.

Hereinbelow, preferred embodiments of the purification method according to the present invention will be described. However, the present invention is not limited to the following embodiments. Specifically, for example, it is preferred that a reaction solution containing PMI produced as described above be separated from the catalyst (separation step), then the step of washing with water at 50° C. or more (water washing step) be repeated three times or more. In the separation step, the separation of the reaction solution containing PMI from the catalyst is not particularly limited, and any known methods, for example, static separation, or cyclone, centrifugation, and thickener, can be used.

In the water washing step, the water used in the washing treatment is not limited to sewage water, pure water, and clean water, and may be slightly alkaline and slightly acid. The amount of water used is not particularly limited and also depends on the concentration of the solution and the like. Specifically, water is used in the amount of 0.5 times or more and more preferably 1 to 5 times by weight ratio, based on aniline used as a raw material. When water is used in the amount as described above, the contents of PPMA and PFA, furthermore APSI and PMA, in the PMI can be sufficiently reduced.

In addition, in the water washing step, it is preferable to wash with water at 50° C. or more. Here, when the temperature of water is less than 50° C. or the amount of water for washing is insufficient (for example, the number of water washing is twice or less), insoluble substance generated in the reaction cannot be sufficiently decomposed and made soluble to water, thus the contents of PPMA and PFA, furthermore APSI and PMA, in the PMI cannot be sufficiently reduced. The temperature of water is preferably over 55° C. and less than 95° C., more preferably 57 to 93° C., and particularly preferably 60 to 90° C. When the temperature difference between the temperature of the reaction solution containing PMI after removing the catalyst and the temperature of the water is large, it is preferred that the reaction solution containing PMI after removing the catalyst be cooled to the same level as the temperature of the water to be added (preferably a temperature of water ±5° C. and more preferably a temperature of water ±3° C.), and then the water washing step be carried out. When the conditions are as described above, the contents of PPMA and PFA, furthermore APSI and PMA, in the PMI can be sufficiently reduced.

The water washing method is not particularly limited, and a method of adding the water to the reaction solution containing PMI after removing the catalyst and stirring the mixture can be preferably used. The water washing treatment can also be carried out by either batch method or continuous method.

The water at a predetermined temperature is added, then the mixture of the layer containing PMI (organic layer) and the aqueous layer is allowed to stand still, whereby the two layers are separated. The aqueous layer is separated from the organic layer. The process from adding water to the reaction solution containing PMI until separating the mixture into the organic layer and the aqueous water is defined as the water washing step. In this water washing step, for example, the number (total number) of water washing in the case of batch method is not particularly limited, and is preferably from 3 to 6 times, and more preferably from 4 to 5 times. When the conditions are as described above, the contents of PPMA and PFA, furthermore APSI and PMA, in the PMI can be sufficiently reduced.

After the water washing step, the organic solvent is distilled away from the organic layer. Here, it is preferred that the water amount in the organic layer before distilling the organic solvent be properly adjusted. Specifically, the water amount in the organic layer before distilling the organic solvent is preferably less than 1% by weight, more preferably 0.05 to 0.99% by weight, and further more preferably 0.5 to 0.98% by weight, based on the content of PMI (crude PMI) in the organic layer (reaction solution layer). Whereby, N-phenylmaleimide in which the contents of PPMA and PFA, furthermore APSI and PMA, in the PMI are reduced can be obtained. In the present specification, "the water amount in the organic layer before distilling the organic solvent" can be calculated as the water amount based on the residue after distilling the solvent from the reaction solution.

According to the above method, an N-phenylmaleimide compound containing 0.1% by weight or less of N-(2,5-dioxo-1-phenyl-3-pyrrolidinyl)-N-phenylmaleamic acid (PPMA) and/or 0.3% by weight or less of N-phenylfumaramic acid (PFA) is obtained. In addition, the total content of the PPMA, PFA, N-phenylmaleamic acid (PMA) and 2-anilino-N-phenylsuccinimide (APSI) in this N-phenylmaleimide compound may be 0.5% by weight or less. As described above, since the content of these impurities in the N-phenylmaleimide compound of the present invention is very low, the copolymer obtained using this N-phenylmaleimide compound can improve the qualities such as appearance, heat resistance and strength.

That is, a second aspect of the present invention relates to a copolymer composition obtained by copolymerizing the N-phenylmaleimide compound and one or more other monomers or resins copolymerizable with the N-phenylmaleimide compound.

The copolymer composition of the present invention is produced using PMI with very low contents of impurities (PPMA, PFA, furthermore PMA, and APSI), thus the contents of these impurities in the copolymer composition are also low.

Specifically, the content of PPMA in the copolymer composition of the present invention is preferably 0.05% by weight or less, more preferably 0.03% by weight or less, more preferably 0.02% by weight or less, and further more preferably less than 0.02% by weight, based on the copolymer composition. Here, when the content of PPMA is as described above, the obtained copolymer composition exhibits excellent qualities such as appearance, heat resistance and strength. Incidentally, the lower limit of the content of PPMA in the copolymer composition as smaller as possible (specifically, 0% by weight) is better. From the industrial viewpoint, the lower limit is normally above 0% by weight, preferably 0.001% by weight or more, and more preferably 0.002% by weight or more.

Also, the content of PFA in the copolymer composition of the present invention is preferably 0.15% by weight or less, more preferably 0.1% by weight or less, further more preferably 0.07% by weight or less, and particularly preferably 0.05% by weight or less, based on the copolymer composition. Here, when the content of PFA is as described above, the obtained copolymer composition exhibits excellent qualities such as appearance, heat resistance and strength. Incidentally, the lower limit of the content of PFA in the copolymer composition as smaller as possible (specifically, 0% by weight) is better. From the industrial viewpoint, the lower limit is normally above 0% by weight, preferably 0.002% by weight or more, and more preferably 0.005% by weight or more.

The content of PMA in the copolymer composition of the present invention is preferably 0.1% by weight or less, more preferably 0.08% by weight or less, further more preferably 0.05% by weight or less, and particularly preferably 0.01% by weight or less, based on the copolymer composition. Here, when the content of PMA is as described above, the obtained copolymer composition exhibits excellent qualities such as appearance, heat resistance and strength. Incidentally, the lower limit of the content of PMA in the copolymer composition as smaller as possible (specifically, 0% by weight) is better. From the industrial viewpoint, the lower limit is normally above 0% by weight, preferably 0.002% by weight or more, and more preferably 0.005% by weight or more.

The content of APSI in the copolymer composition of the present invention is preferably 0.1% by weight or less, more preferably 0.06% by weight or less, further more preferably 0.04% by weight or less, and particularly preferably 0.025% by weight or less, based on the copolymer composition. Here, when the content of APSI is as described above, the obtained copolymer composition exhibits excellent qualities such as appearance, heat resistance and strength. Incidentally, the lower limit of the content of APSI in the copolymer composition as smaller as possible (specifically, 0% by weight) is better. From the industrial viewpoint, the lower limit is normally above 0% by weight, preferably 0.002% by weight or more, and more preferably 0.005% by weight or more.

The total content of PMA, APSI, PPMA and PFA in the copolymer composition of the present invention is preferably 0.25% by weight or less, more preferably 0.2% by weight or less, further more preferably 0.15% by weight or less, still further more preferably 0.1% by weight or less, and particularly preferably 0.05% by weight or less, based on the copolymer composition. Here, when the total content of PMA, APSI, PPMA and PFA is as described above, the obtained copolymer composition exhibits excellent qualities such as appearance, heat resistance and strength. Incidentally, the lower limit of the total content of PMA, APSI, PPMA and PFA in the copolymer composition as smaller as possible (specifically, 0% by weight) is better. From the industrial viewpoint, the lower limit is normally above 0% by weight and preferably 0.005% by weight or more.

The copolymer composition of the present invention is obtained by copolymerizing an N-phenylmaleimide compound (PMI) and one or more other monomers or resins copolymerizable with the N-phenylmaleimide compound. Here, the monomer other than the PMI (other monomer) used as a production raw material is not particularly limited as long as the monomer is copolymerizable with PMI. Specifically, other monomer includes maleimide compounds (except for N-phenylmaleimide), (meth)acrylates, aromatic vinyls, unsaturated nitriles, olefins, dienes, vinyl ethers, vinyl esters, vinyl fluorides, allyl esters or (meth)acrylic acid esters of saturated aliphatic monocarboxylic acids such as allyl propionate, poly(meth)acrylates, polyarylates, glycidyl compounds, unsaturated carboxylic acids, and the like. Among the above compounds, (meth)acrylates, aromatic vinyls, and unsaturated nitriles are particularly preferable.

Here, the other monomers described above may be used singly or in the form of a mixture of two or more thereof.

The maleimide compounds are not particularly limited, and examples include N-alkylmaleimides such as N-methylmaleimide, N-ethylmaleimide, N-hexylmaleimide, N-octylmaleimide and N-dodecylmaleimide; N-benzylmaleimide; N-cycloalkylmaleimides such as N-cyclohexylmaleimide; N-substituted phenylmaleimides being substituted by a nitro group, an alkoxy group, an alkyl group, a carboxyl group, a hydroxyl group, a halogen atom or the like such as N-nitrophenylmaleimide, N-methoxyphenylmaleimide, N-methylphenylmaleimide, N-carboxyphenylmaleimide, N-hydroxyphenylmaleimide, N-chlorophenylmaleimide, N-dimethylphenylmaleimide, N-dichlorophenylmaleimide, N-bromophenylmaleimide, N-dibromophenylmaleimide, N-trichlorophenylmaleimide, and N-tribromophenylmaleimide; and the like. Comprehensively considering availability and physical properties of the obtained copolymer, N-cyclohexylmaleimide and N-benzylmaleimide are preferably used. Here, plural types of these maleimide compounds can be used in combination.

The (meth)acrylates are not particularly limited, and for example, (meth)acrylic acid esters having any of alkyl groups having 1 to 18 carbons, cyclohexyl groups, and benzyl groups as the ester group are suitable. Specifically, the (meth)acrylic acid esters include methyl (meth)acrylate, ethyl (meth)acrylate, propyl (meth)acrylate, isopropyl (meth)acrylate, butyl (meth)acrylate, isobutyl (meth)acrylate, tert-butyl (meth)acrylate, amyl (meth)acrylate, 2-ethylhexyl (meth)acrylate, cyclohexyl (meth)acrylate, benzyl (meth)acrylate, and the like. Among them, methyl methacrylate is preferable. Here, plural types of these (meth)acrylates can be used in combination.

The aromatic vinyls are not particularly limited, and examples include styrene, α-methylstyrene, p-methylstyrene, isopropenylstyrene, vinyl toluene, chlorostyrene, and the like. Among them, styrene is particularly preferable. The unsaturated nitriles are not particularly limited, and examples include acrylonitrile, methacrylonitrile, phenylacrylonitrile, and the like.

The olefins are not particularly limited, and examples include ethylene, propylene, isobutylene, diisobutylene, and the like. The dienes are not particularly limited, and examples include butadiene, isoprene, and the like. The vinyl ethers are not particularly limited, and examples include methyl vinyl ether, butyl vinyl ether, and the like.

The vinyl esters are not particularly limited, and examples include vinyl acetate, vinyl propionate, and the like. The vinyl fluorides are not particularly limited, and examples include vinylidene fluoride and the like. The poly(meth)acrylates are not particularly limited, and examples include ethylene glycol di(meth)acrylate, diethylene glycol di(meth)acrylate, divinylbenzene, diallyl phthalate, trimethylolpropane tri(meth)acrylate, hexanediol di(meth)acrylate, pentaerythritol tetra(meth)acrylate, dipentaerythritol hexa(meth)acrylate, di(meth)acrylates adducted ethylene oxide or propylene oxide of bisphenol A, di(meth)acrylates adducted ethylene oxide or propylene oxide of halogenated bisphenol A, di or tri(meth)acrylates adducted ethylene oxide or propylene oxide of isocyanurate, and the like.

The polyarylates are not particularly limited, and examples include tolyl isocyanurate and the like. The glycidyl compounds are not particularly limited, and examples include glycidyl(meth)acrylate, allyl glycidyl ether, and the like. The unsaturated carboxylic acids are not particularly limited, and examples include acrylic acid, methacrylic acid, itaconic acid, maleic acid, fumaric acid, or hemi-esterified products or anhydrides thereof.

In addition, similarly, the resins used as a production raw material are not particularly limited as long as the monomer is copolymerizable with PMI. Specifically, the resins include ABS resins (acrylonitrile-butadiene-styrene copolymers), AS resins (acrylonitrile-styrene copolymers), AB resins (acrylonitrile-butadiene copolymers), ACS resins (acrylonitrile-chlorinated polyethylene-styrene copolymers), AES resins (acrylonitrile-ethylene propylene rubber-styrene copolymers), AAS resins (acrylonitrile-acrylic rubber-styrene copolymers), polystyrene, polyacrylonitrile, polyvinyl chloride, polyvinylidene chloride, polymethyl methacrylate, phenol resins, natural rubbers, butadiene rubbers, isoprene rubbers, butyl rubber, styrene-butadiene rubbers, chloroprene rubbers, and the like. Among them, AB resins, ABS resins, AS resins and butadiene rubbers are preferable. Here, the above resins may be used singly or in the form of a mixture of two or more thereof. Alternatively, one or more of the above resins may be used in combination with one or more of the other monomers described above.

The amounts of the other monomers and the resins (the total amount of the other monomers and the resins) are preferably 50 to 95% by weight and further preferably 60 to 90% by weight. When the amount is less than 50% by weight, the viscosity is increased when melting the obtained copolymer, and it is likely to be disadvantageous in the aspect of molding processability. Also, when the amount is over 95% by weight, heat resistance is unlikely to increase. That is, when the copolymer composition according to the present invention is produced, the amount of the N-phenylmaleimide compound in the entire copolymerizing raw materials is preferably 5 to 50% by weight and further preferably 10 to 40% by weight. When the amount is as described above, heat resistance by N-phenylmaleimide can be sufficiently increased.

In addition, examples of the monomer copolymerizable with these monomers include fumaronitrile, isopropyl fumarate, acenaphthylene, and the like. The copolymerizable monomer is an optionally added component, and may not be used as a production raw material in the present invention. When the copolymerizable monomer is used, it can be used in the range of 0 to 30% by weight.

A chain-transfer agent can be used in order to control the molecular weight of the (co)polymer. Here, the chain-transfer agent is not particularly limited, and examples include alkyl mercaptans such as butyl mercaptan, octyl mercaptan and tert-dodecyl mercaptan, α-styrene dimer, and the like. Furthermore, according to the intended application and required performance of the obtained copolymer resin, various additives such as an ultraviolet absorber and a stabilizer can also be added.

When PMI of the present invention is copolymerized with one or more of other monomers or resins, a polymerization initiator can be used. The polymerization initiator that can be herein used is not particularly limited, and an organic peroxide-based polymerization initiator and an azo-based polymerization initiator can be preferably used. The organic peroxide-based polymerization initiator includes benzoyl peroxide, lauroyl peroxide, methyl ethyl ketone peroxide, tert-butyl peroxyoctoate, tert-butyl peroxybenzoate, tert-butyl peroxy-2-ethylhexanoate, tert-hexyl peroxy isopropyl monocarbonate, tert-hexylperoxy-2-ethylhexanoate, tert-amylperoxy-2-ethylhexanoate, cumene hydroperoxide, cyclohexanone peroxide, dicumyl peroxide, bis(4-tert-butylcyclohexyl)peroxydicarbonate, tert-butylperoxyisopropyl carbonate, 1,1-bis(tert-hexylperoxy)-3,3,5-trimethylcyclohexane, lauroyl peroxide, and the like. The azo-based polymerization initiator includes 2,2'-azobisisobutyronitrile, 2,2'-azobis(2-methylbutyronitrile), 1,1'-azobis(cyclohexane-1-carbonitrile), 2-phenylazo-2,4-dimethyl-4-methoxyvaleronitrile, and the like. As the polymerization initiator, those having a half-life temperature (1 hour half-life temperature) of 60 to 140° C. or so are preferable, and those having a half-life temperature of 80° C. to 120° C. or so are more preferable. These polymerization initiators may be used singly, or plural types can be used in combination.

As the method of copolymerization reaction, batch polymerization methods such as suspension, emulsion and bulk may be adopted by previously adding a predetermined amount of multifunctional aromatic monomers such as divinylbiphenyl as necessary, at the same time as raw material monomers (PMI, other monomers and/or resins), a polymerization initiator, and polymerization aids such as a chain-transfer agent and a dispersant as necessary, and the like. Alternatively, continuous polymerization methods such as bulk polymerization and solution polymerization may be adopted by continuously feeding a solution obtained by dissolving a predetermined amount of multifunctional aromatic monomers such as divinylbiphenyl in the raw material monomers to the polymerization system. For example, when only thermal polymerization is carried out without using a polymerization initiator in the bulk batch polymerization and bulk or solution continuous polymerization, a polymerization temperature of 130° C. or more is preferable for the purpose of production improvement. However, when polymerization is carried out by the method as described above, by-product of an oligomer could be generated. Therefore, it is preferable to add a polymerization initiator such as organic peroxide-based and azo-based in an amount of 50 to 2000 ppm based on the raw materials and lower the polymerization temperature, to perform polymerization.

The polymerization temperature in this case is not particularly limited, and is preferably 70 to 160° C. or so, which is higher than the 1 hour half-life temperature ($T_1$) of the polymerization initiator by 5 to 20° C. or so, and more preferably 80 to 140° C. or so. When the polymerization temperature is less than 70° C., a load of the volatilization step of removing unreacted monomers and solvent is increased, and the remaining monomers and remaining solvent are increased, thus it is not preferable in quality. In addition, when the polymerization temperature is above 160° C., it is not preferable since the control of polymerization reaction becomes impossible and the hue is deteriorated. In the case of suspension and emulsification polymerizations, the polymerization temperature is preferably 70 to 90° C. and particularly preferably 75 to 85° C. In this case, an organic peroxide-based initiator or azo-based initiator is used together with an emulsifier and a surfactant. The types of the organic peroxide-based initiator or azo-based initiator, the emulsifier and the surfactant are not particularly limited. In addition, the polymerization time is not particularly limited, and is preferably 0.5 to 10 hours or so and more preferably 1 to 5 hours or so. Here, the polymerization may be carried out under a single condition, or may be carried out under different conditions in plural times. Regarding the polymerization temperature and polymerization time in the latter case, it is preferred that the conditions in each polymerization operation be in the above ranges.

Alternatively, after the polymerization operations, as necessary, the obtained copolymer composition may be desolvated by steam distillation, pulverized, and dried, then allowed to pass through an extruder, to collect a copolymer resin as pellets.

The copolymer composition obtained as described above may directly be practiced singly, and it is preferable to further blend the copolymer with a rubber-modified graft copolymer such as an ABS resin, an AES resin, or an AAS resin since the copolymer can be formed into a resin composition having further excellent heat resistance and impact resistance.

The copolymer composition obtained as described above can be further molded into a desired shape by a conventionally used molding method such as extrusion molding and injection molding, for the purpose of using in the various intended uses as described above.

EXAMPLES

Hereinbelow, the present invention will be described in further detail with reference to examples. However, the present invention is not limited only to these examples. Unless otherwise noted, "part" means "part by weight", and "%" means "% by weight".

(Methods for Analyzing PMI and Contained Material)

The purity of PMI was measured using a high-performance liquid chromatography (HPLC, manufactured by Shimadzu Corporation, model number: LC-10A), and also the content was measured by separating each contained material. The conditions are as described below.

[Chemical Formula 7]
Column: ZORBAX C18 (manufactured by SHIMADZU GLC Ltd.)
Mobile phase: a mixed solution of an aqueous solution of potassium dihydrogen orthophosphate (0.0085 mol/l) and methanol (mixing ratio: 2.4/1.0 (wt/wt)) (adjusted to pH 3.7 with orthophosphoric acid)
Column temperature: 45° C.
Flow rate: 0.8 ml/min Here, the contents of PPMA, PFA, PMA and APSI in the copolymer composition were measured by gas chromatograph mass spectrometry (GC-MS) under the following conditions.

[Chemical Formula 8]
Pyrolysis Conditions
Apparatus: JCP-22 portable pyrolyzer (manufactured by Japan Analytical Industry Co., Ltd.)
Conditions: 500° C.×10 seconds
GC-MS Conditions
Apparatus: MSroute600W (manufactured by JEOL Ltd.)
Measurement mode: EI method 70 eV
INLET PIPE, GC INTERFACE, ion source temperature: 250° C.
Column: DB-1 50 m×0.32 mm 0.5 µm
Column temperature: retained at 50° C. for 1 minute, heated to 270° C. at 15° C./min, then retained for 14 minutes
INJ temperature: 250° C.

Example 1

To a 200 cc beaker was added 20 g of orthophosphoric acid, followed by adding a granular silica gel carrier (CARiACT 30; trade name, manufactured by Fuji Davison Chemical Ltd.) to support orthophosphoric acid. To a flask equipped with a thermometer, a condenser equipped with a water separator, a dropping funnel and a stirrer was charged a solution obtained by dissolving 55 g of maleic anhydride in 50 g of xylene. Next, the temperature inside the flask was adjusted to 80° C., and a solution obtained by dissolving 50 g of aniline in 400 g of xylene was gradually added thereto over 30 minutes, to synthesize a xylene slurry liquid of N-phenylmaleamic acid. To the obtained slurry liquid was added a catalyst previously prepared in a beaker and 0.1 g of copper dibutyldithiocarbamate, and the mixture was reacted at 140° C. for 3 hours. After the completion of the reaction, the reaction solution was separated from the catalyst layer. The separated reaction solution was cooled to 85 to 90° C., 150 g of pure water at 87° C. was added to this reaction solution, and the mixture was stirred for 5 minutes. Next, when the stirring was stopped, the mixture immediately separated into the reaction solution layer and the aqueous layer. In addition, the interface between the both layers was very clear, and thus the separation of the both layers was easy. Subsequently, this operation was repeated further three times. In this third operation, the mixture was retained for 30 minutes as the static time for separation into the reaction solution layer and the aqueous layer, and after oil and water separation, the water amount in the obtained reaction solution layer was 0.8 g (0.87(=0.8/92) % by weight, based on PMI in the reaction solution layer). Xylene was distilled away from this reaction solution layer to obtain 92 g of yellow crystal. Next, this crystal was distilled at 160° C. under a reduced pressure of 3 mmHg to obtain 85 g of bright yellow crystal of an N-phenylmaleimide compound. The result of analyzing the components of the obtained N-phenylmaleimide compound is shown in Table 1.

Comparative Example 1

The same procedures were carried out as in Example 1, except for performing only once the separation operation that was repeatedly performed in Example 1, to obtain an N-phenylmaleimide compound. The analytical result of the obtained N-phenylmaleimide compound is shown in Table 1.

Comparative Example 2

The same procedures were carried out as in Example 1, except for retaining in the third separation for 5 minutes as the static time in Example 1, to obtain 82 g of an N-phenylmaleimide compound. At this time, after separating the reaction solution layer and the aqueous layer, the water amount in the obtained reaction solution layer was 1.3 g (1.41(=1.3/92) % by weight, based on PMI in the reaction solution layer). The result of analyzing the components of the obtained N-phenylmaleimide compound is shown in Table 1.

Example 2

The same procedures were carried out as in Example 1, except that, after the completion of the reaction in Example 1, the reaction solution was separated from the catalyst layer, the separated reaction solution was cooled to 90 to 95° C., 150 g of pure water at 95° C. was added to this reaction solution, and the mixture was stirred for 5 minutes, to obtain 84 g of an N-phenylmaleimide compound. At this time, after separating the reaction solution layer and the aqueous layer, the water amount in the obtained reaction solution layer was 0.9 g (0.98(=0.9/92) % by weight, based on PMI in the reaction solution layer). The result of analyzing the components of the obtained N-phenylmaleimide compound is shown in Table 1.

Example 3

The same procedures were carried out as in Example 1, except that, after the completion of the reaction in Example 1, the reaction solution was separated from the catalyst layer, the separated reaction solution was cooled to 55 to 60° C., 150 g of pure water at 55° C. was added to this reaction solution, and the mixture was stirred for 5 minutes, to obtain 78 g of an N-phenylmaleimide compound. At this time, after separating the reaction solution layer and the aqueous layer, the water amount in the obtained reaction solution layer was 0.6 g (0.65(=0.6/92) % by weight, based on PMI in the reaction solution layer). The result of analyzing the components of the obtained N-phenylmaleimide compound is shown in Table 1.

Example 4

The same procedures were carried out as in Comparative Example 1, except that, when the catalyst and copper dibutyldithiocarbamate were added to the xylene slurry liquid of N-phenylmaleamic acid and the mixture was reacted at 140° C. in Comparative Example 1, a solution obtained by dissolving 10 g of maleic anhydride in 15 g of xylene was added after 30 minutes from the start of the reaction, to obtain an N-phenylmaleimide compound. The analytical result thereof is shown in Table 1.

Example 5

The same procedures were carried out as in Example 1, except that, when the catalyst and copper dibutyldithiocarbamate were added to the xylene slurry liquid of N-phenylmaleamic acid and the mixture was reacted at 140° C. in Example 1, a solution obtained by dissolving 10 g of maleic anhydride in 15 g of xylene was added after 30 minutes from the start of the reaction, to obtain an N-phenylmaleimide compound. The analytical result thereof is shown in Table 1.

Example 6

Inside a polymerization vessel having an internal volume of 30 liters equipped with ribbon impellers was replaced with nitrogen, thereto were charged 20 parts by weight of butadiene rubber (BR01; trade name, manufactured by JSR Corporation), 20 parts by weight of the N-phenylmaleimide compound obtained in Example 1, 15 parts by weight of acrylonitrile and 100 parts by weight of toluene, and the mixture was stirred at 50° C. until the butadiene rubber and the N-phenylmaleimide compound were completely dissolved. Subsequently, 45 parts by weight of styrene, 0.1 part by weight of tert-dodecyl mercaptan and 0.4 parts by weight of benzoyl peroxide were added thereto, and then the mixture was heated and polymerized at 100° C. for 2.2 hours, and further heated and polymerized at 120° C. for 2.2 hours. The polymerization conversion rate was 98%. After completion of polymerization, the obtained mixture may be desolvated by steam distillation, pulverized, and dried, then allowed to pass through an extruder with 40 mmφ at a temperature of 240° C., to collect a copolymer resin as pellets. The obtained copolymer resin was melted and mixed by the extruder, then injection molded to prepare a test piece, and the physical properties were measured. Incidentally, heat distortion temperature and Izod impact strength were measured in accordance with "ASTM D648" and "ASTM D256", respectively. The result of measuring physical properties is shown in Table 2, along with visual appearance.

In addition, the contents of PPMA, PFA, PMA and APSI in the copolymer resin (copolymer composition) obtained by the polymerization were measured. The result is shown in Table 2.

Example 7

The polymerization was carried out in the same manner as in Example 6, except for using the N-phenylmaleimide compound obtained in Example 2, to obtain a copolymer resin (copolymer composition). The result of measuring physical properties is shown in Table 2.

In addition, the contents of PPMA, PFA, PMA and APSI in the copolymer resin obtained by the polymerization were measured. The result is shown in Table 2.

Example 8

The polymerization was carried out in the same manner as in Example 6, except for using the N-phenylmaleimide compound obtained in Example 3, to obtain a copolymer resin (copolymer composition). The result of measuring physical properties is shown in Table 2.

In addition, the contents of PPMA, PFA, PMA and APSI in the copolymer resin obtained by the polymerization were measured. The result is shown in Table 2.

Example 9

The polymerization was carried out in the same manner as in Example 6, except for using the N-phenylmaleimide compound obtained in Example 4, to obtain a copolymer resin (copolymer composition). The result of measuring physical properties is shown in Table 2.

In addition, the contents of PPMA, PFA, PMA and APSI in the copolymer resin obtained by the polymerization were measured. The result is shown in Table 2.

Example 10

The polymerization was carried out in the same manner as in Example 6, except for using the N-phenylmaleimide compound obtained in Example 5, to obtain a copolymer resin (copolymer composition). The result of measuring physical properties is shown in Table 2.

In addition, the contents of PPMA, PFA, PMA and APSI in the copolymer resin obtained by the polymerization were measured. The result is shown in Table 2.

Comparative Examples 3 to 4

The polymerization was carried out in the same manner as in Example 6, except for using the N-phenylmaleimide compounds obtained in Comparative Examples 1 to 2, to obtain a copolymer resin (copolymer composition). The result of measuring physical properties is shown in Table 2.

In addition, the contents of PPMA, PFA, PMA and APSI in the copolymer obtained by the polymerization were measured. The result is shown in Table 2.

TABLE 1

| | PMI [% by weight] | PPMA [% by weight] | PFA [% by weight] | PMA [% by weight] | APSI [% by weight] |
|---|---|---|---|---|---|
| PMI Example 1 | 99.7 | 0.06 | 0.014 | 0.008 | 0.08 |
| PMI Comparative Example 1 | 99.3 | 0.12 | 0.31 | 0.010 | 0.23 |
| PMI Comparative Example 2 | 98.7 | 0.11 | 0.38 | 0.43 | 0.32 |
| PMI Example 2 | 99.4 | 0.07 | 0.30 | 0.030 | 0.10 |
| PMI Example 3 | 99.5 | 0.10 | 0.25 | 0.022 | 0.12 |
| PMI Example 4 | 99.7 | 0.08 | 0.08 | 0.009 | 0.11 |
| PMI Example 5 | 99.8 | 0.02 | 0.06 | 0.008 | 0.05 |

*PMI = N-phenylmaleimide,
PPMA = N-(2,5-dioxo-1-phenyl-3-pyrrolidinyl)-N-phenylmaleamic acid,
PFA = N-phenylfumaramic acid,
PMA = N-phenylmaleamic acid,
APSI = 2-anilino-N-phenylsuccinimide

TABLE 2

| | Appearance*[1] | Heat distortion temperature (° C.) | Izod impact strength (kg · cm/cm) | Content (% by weight) | | | |
|---|---|---|---|---|---|---|---|
| | | | | PPMA | PFA | PMA | APSI |
| Copolymer Example 6 | ◉ | 119 | 11 | 0.012 | 0.003 | 0.002 | 0.016 |
| Copolymer Comparative Example 3 | X | 116 | 7 | 0.024 | 0.062 | 0.002 | 0.046 |
| Copolymer Comparative Example 4 | X | 115 | 6 | 0.022 | 0.076 | 0.086 | 0.064 |
| Copolymer Example 7 | ○ | 117 | 8 | 0.014 | 0.060 | 0.006 | 0.020 |
| Copolymer Example 8 | ○ | 117 | 9 | 0.020 | 0.050 | 0.004 | 0.024 |
| Copolymer Example 9 | ○ | 118 | 10 | 0.016 | 0.016 | 0.002 | 0.022 |
| Copolymer Example 10 | ◉ | 121 | 13 | 0.004 | 0.012 | 0.002 | 0.010 |

*◉ no uneven color, silver streak and fish eye ○: very slightly uneven color, no silver streak and fish eye X: some uneven color, some silver streak, and no fish eye

INDUSTRIAL APPLICABILITY

According to the method of the present invention, a copolymer obtained using N-phenylmaleimide as at least one component of the copolymerization monomers, in which phenomena such as coloring, silver streak and fish eye are reduced, thus the qualities (appearance, heat resistance, and strength) are improved, can be efficiently produced.

In addition, the present application is based on Japanese Patent Application No. 2011-065547 filed on Mar. 24, 2011, the disclosure of which is incorporated herein by reference.

The invention claimed is:

1. A copolymer composition obtained by copolymerizing an N-phenylmaleimide compound and one or more other monomers or resins copolymerizable with the N-phenylmaleimide compound,
    wherein the N-phenylmaleimide compound comprises 0.005 to 0.08% by weight of N-(2,5-dioxo-1-phenyl-3-pyrrolidinyl)-N-phenylmaleamic acid (PPMA) and 0.01 to 0.08% by weight of N-phenylfumaramic acid (PFA),
    wherein the contents of the PPMA and PFA are measured using a high-performance liquid chromatography under conditions as below:
Mobile phase: a mixed solution of an aqueous solution of potassium dihydrogen orthophosphate (0.0085 mol/l) and methanol (mixing ratio: 2.4/1.0 (wt/wt)) adjusted to a pH of 3.7 with orthophosphoric acid;
Column temperature: 45° C.;
Flow rate: 0.8 ml/min.

2. The copolymer composition according to claim 1, comprising 0.05% by weight or less of N-(2,5-dioxo-1-phenyl-3-pyrrolidinyl)-N-phenylmaleamic acid (PPMA).

3. The copolymer composition according to claim 1, comprising 0.15% by weight or less of N-phenylfumaramic acid (PFA).

4. The copolymer composition according to claim 1, wherein an acrylonitrile-butadiene copolymer (AB resin), an acrylonitrile-butadiene-styrene copolymer (ABS resin) or an acrylonitrile-styrene copolymer (AS resin) is obtained by the copolymerization.

5. A copolymer composition obtained by copolymerizing an N-phenylmaleimide compound and one or more other monomers or resins copolymerizable with the N-phenylmaleimide compound,
    wherein the N-phenylmaleimide compound comprises 0.005 to 0.08% by weight of N-(2,5-dioxo-1-phenyl-3-pyrrolidinyl)-N-phenylmaleamic acid (PPMA) and 0.01 to 0.08% by weight of N-phenylfumaramic acid (PFA),
    wherein the N-phenylmaleimide compound further comprises N-phenylmaleamic acid (PMA) and 2-anilino-N-phenylsuccinimide (APSI),
    wherein the total content of the PMA, APSI, PPMA and PFA in the N-phenylmaleimide compound is 0.1 to 0.5% by weight,
    wherein the contents of the PPMA, PFA, PMA, and APSI are measured using a high-performance liquid chromatography under conditions as below:
Mobile phase: a mixed solution of an aqueous solution of potassium dihydrogen orthophosphate (0.0085 mol/l) and methanol (mixing ratio: 2.4/1.0 (wt/wt)) adjusted to pH of 3.7 with orthophosphoric acid;
Column temperature: 45° C.;
Flow rate: 0.8 ml/min.

6. The copolymer composition according to claim 2, comprising 0.15% by weight or less of N-phenylfumaramic acid (PFA).

7. The copolymer composition according to claim 2, wherein an acrylonitrile-butadiene copolymer (AB resin), an acrylonitrile-butadiene-styrene copolymer (ABS resin) or an acrylonitrile-styrene copolymer (AS resin) is obtained by the copolymerization.

8. The copolymer composition according to claim 3, wherein an acrylonitrile-butadiene copolymer (AB resin), an acrylonitrile-butadiene-styrene copolymer (ABS resin) or an acrylonitrile-styrene copolymer (AS resin) is obtained by the copolymerization.

9. The copolymer composition according to claim 1, comprising 0.004 to 0.020% by weight of N-(2,5-dioxo-1-phenyl-3-pyrrolidinyl)-N-phenylmaleamic acid (PPMA) and 0.003 to 0.060% by weight of N-phenylfumaramic acid (PFA).

10. The copolymer composition according to claim 5, comprising 0.004 to 0.020% by weight of N-(2,5-dioxo-1-phenyl-3-pyrrolidinyl)-N-phenylmaleamic acid (PPMA) and 0.003 to 0.060% by weight of N-phenylfumaramic acid (PFA).

11. The copolymer composition according to claim 6, wherein an acrylonitrile-butadiene copolymer (AB resin), an acrylonitrile-butadiene-styrene copolymer (ABS resin) or an acrylonitrile-styrene copolymer (AS resin) is obtained by the copolymerization.

12. The copolymer composition according to claim 1, wherein the N-phenylmaleimide compound is obtained by a purification process comprising separating a reaction solution containing N-phenylmaleimide from a catalyst, and washing the resulting compound containing N-phenylmaleimide three times or more with water at a temperature of 50° C. or greater.

13. A compound, comprising N-phenylmaleimide,
    wherein the compound further comprises 0.005 to 0.08% by weight of N-(2,5-dioxo-1-phenyl-3-pyrrolidinyl)-N-phenylmaleamic acid (PPMA) and 0.01 to 0.08% by weight of N-phenylfumaramic acid (PFA),
    wherein the total content of the PPMA, PFA, N-phenylmaleamic acid (PMA), and 2-anilino-N-phenylsuccinimide (APSI) in the compound is 0.1 to 0.5% by weight,
    wherein the contents of the PPMA, PFA, PMA, and APSI are measured using a high-performance liquid chromatography under conditions as below:
Mobile phase: a mixed solution of an aqueous solution of potassium dihydrogen orthophosphate (0.0085 mol/l) and methanol (mixing ratio: 2.4/1.0 (wt/wt)) adjusted to a pH of 3.7 with orthophosphoric acid;
Column temperature: 45° C.;
Flow rate: 0.8 ml/min.

14. The compound according to claim 13, wherein the compound is obtained by a purification process comprising separating a reaction solution containing N-phenylmaleimide from a catalyst, and washing the resulting compound containing N-phenylmaleimide three times or more with water at a temperature of 50° C. or greater.

15. A method of obtaining the compound according to claim 13, the method comprising:
    separating a reaction solution containing N-phenylmaleimide from a catalyst, and
    washing the resulting compound containing N-phenylmaleimide three times or more with water at a temperature of 50° C. or greater.

16. The copolymer composition according to claim 1, wherein a total content of PPMA and PFA of the N-phenyl-maleimide compound is less than or equal to 0.08% by weight.

* * * * *